(12) United States Patent
Engelson et al.

(10) Patent No.: US 6,221,061 B1
(45) Date of Patent: *Apr. 24, 2001

(54) LUBRICIOUS CATHETERS

(75) Inventors: Erik T. Engelson, Menlo Park; Robert Hergenrother, Fremont; Joseph Eder, Los Altos, all of CA (US)

(73) Assignee: Target Therapeutics, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/601,186

(22) Filed: Feb. 14, 1996

Related U.S. Application Data

(63) Continuation of application No. 08/060,401, filed on May 12, 1993, now Pat. No. 5,531,715.

(51) Int. Cl.⁷ .................................................. A61M 25/00

(52) U.S. Cl. ............................................................ 604/265

(58) Field of Search .................................... 604/264–266, 604/523, 524, 525, 270; 520/329.7; 427/457, 487

(56) References Cited

U.S. PATENT DOCUMENTS

| | | |
|---|---|---|
| 4,055,682 | 10/1977 | Merrill . |
| 4,326,532 | 4/1982 | Hammar . |
| 4,331,783 | 5/1982 | Stoy . |
| 4,337,327 | 6/1982 | Stoy . |
| 4,369,294 | 1/1983 | Stoy . |
| 4,370,451 | 1/1983 | Stoy . |
| 4,373,009 | 2/1983 | Winn . |
| 4,379,874 | 4/1983 | Stoy . |
| 4,407,855 | 10/1983 | Russell . |
| 4,420,589 | 12/1983 | Stoy . |
| 4,503,126 | 3/1985 | Phillips et al. . |
| 4,526,579 | 7/1985 | Ainpour . |
| 4,589,873 | 5/1986 | Schwartz et al. . |
| 4,668,224 | 5/1987 | Lentz et al. . |
| 4,722,906 | 2/1988 | Guire . |
| 4,739,768 | 4/1988 | Engelson . |
| 4,773,902 | 9/1988 | Lentz et al. . |
| 4,784,651 | 11/1988 | Hickey . |
| 4,838,876 | 6/1989 | Wong et al. . |
| 4,846,812 | 7/1989 | Walker et al. . |
| 4,884,579 | 12/1989 | Engelson . |
| 4,906,237 | 3/1990 | Johansson et al. . |

(List continued on next page.)

FOREIGN PATENT DOCUMENTS

| | | |
|---|---|---|
| 0166998 | 1/1986 | (EP) . |
| 0389632 | 10/1990 | (EP) . |
| 6909499 | 2/1970 | (NL) . |

OTHER PUBLICATIONS

Nagaoka, S., et al., "Newly developed hdrophilic slippery surface for medical application" High Performance Biomaterials (1991) pp. 475–481.

FasTRACKER–18™ Micro–Infusion Catheter, Draft Product Brochure (7 pages total), Target Therapeutics, Inc.,47201 Lakeview Blvd., Fremont CA, 94537.

Zephyr Flow–Assisted Infusion Catheter, Draft Product Brochure (4 pages total), Target Therapeutics, Inc.,47201 Lakeview Blvd., Fremont CA, 94537.

*Primary Examiner*—Anhtuan T. Nguyen
(74) *Attorney, Agent, or Firm*—Morrison & Foerster LLP

(57) ABSTRACT

This invention is in the general field of surgical instruments. It relates specifically to catheters which may be used in cardiovascular and endovascular procedures to deliver diagnostic, therapeutic, or vaso-occlusive agents to a target site within a human or animal body which is accessible by a system of natural passageways within that body. The catheters are coated in such a way that they are exceptionally slippery and the coating is very durable. The invention also relates to methods of coating the catheters and to methods of applying lubricious coatings.

11 Claims, 2 Drawing Sheets

U.S. PATENT DOCUMENTS

| | | |
|---|---|---|
| 4,943,618 | 7/1990 | Stoy et al. . |
| 4,968,532 | 11/1990 | Janssen et al. . |
| 4,973,493 | 11/1990 | Guire . |
| 4,979,959 | 12/1990 | Guire . |
| 5,001,009 * | 3/1991 | Whitbourne ............ 428/412 |
| 5,002,582 | 3/1991 | Guire et al. . |
| 5,004,461 * | 4/1991 | Wilson ................. 604/265 |
| 5,061,738 | 10/1991 | Solomon et al. . |
| 5,069,673 | 12/1991 | Shwab . |
| 5,084,033 | 1/1992 | O'Neill et al. . |
| 5,135,516 * | 8/1992 | Sahatjian et al. ........ 604/265 |
| 5,147,315 | 9/1992 | Weber . |
| 5,171,232 | 12/1992 | Castillo et al. . |
| 5,234,416 | 8/1993 | Macauley et al. . |
| 5,272,012 | 12/1993 | Opolski . |
| 5,286,382 | 2/1994 | Scarmoutzos et al. . |
| 5,300,048 | 4/1994 | Drewes, Jr. et al. . |
| 5,314,418 | 5/1994 | Takano et al. . |
| 5,331,027 * | 7/1994 | Whitbourne ............ 604/265 X |
| 5,401,257 * | 3/1995 | Chevalier et al. ........ 604/265 |
| 5,531,715 * | 7/1996 | Engelson et al. ........ 604/265 |

* cited by examiner

LUBRICIOUS CATHETERS

This application is a continuation of application Ser. No. 08/060,401 filed May 12, 1992 now U.S. Pat. No. 5,531,715.

FIELD OF THE INVENTION

This invention is in the general field of surgical instruments. It relates specifically to catheters which may be used in cardiovascular and endovascular procedures to deliver diagnostic, therapeutic, or vaso-occlusive agents or devices to a target site within a human or animal body which is accessible by a system of natural passageways within that body. The catheters are coated in such a way that they are exceptionally slippery and the coating is very durable. The invention also relates to methods for coating the catheters and to methods for applying lubricious coatings.

BACKGROUND OF THE INVENTION

Catheters are increasingly used to deliver diagnostic or therapeutic agents and devices to internal target sites that can be accessed through the circulatory or other system. There are a number of general approaches for placing catheters within vessels in the body to reach target sites that are difficult to access. In one technique, a torqueable guidewire is introduced into the vasculature and, using radiography to monitor its advance through the body's passageways, is rotated to allow the guidewire's bent guide tip to follow a chosen route (when a choice of pathways is found) and advanced towards the target site. At chosen intervals during the guidewire's advancement, the catheter is slid along the guidewire until the distal end of the catheter approaches the distal end of the guidewire. This procedure is repeated until the distal end of the catheter is positioned at the target site. An example of this technique is described in U.S. Pat. No. 4,884,579. This is a widely accepted and respected method for approaching target sites in complicated area of the vasculature. It, however, has the drawback of being somewhat time-consuming due to the necessity of rotating and advancing the guidewire and catheter through the vasculature.

A second technique for advancing a catheter to a target site is to use the blood flow as the motive force in placing the distal end of the catheter at the desired target site. Such methods often employ a highly flexible catheter having an inflatable, but pre-punctured balloon at its distal end. In use, the balloon is partially inflated, and carried by blood flow into the target site. During placement, the balloon is continually inflated to replenish fluid leaking from the balloon. This technique, too, has drawbacks including the fact that at least the distal portion of the catheter is so floppy that it cannot be pushed without buckling. Instead the catheter must be advanced using injected fluid to inflate the balloon to propel the catheter to the target site. Additionally, there is a risk of rupture of a vessel by a balloon that has been overinflated.

In order to address some of the above described problems, another approach has involved the use of flexible catheters having extremely flexible distal portions which can be directed to a target site using the blood flowing to that site as the motive force but without the use of balloons on the distal catheter tip. These flow-directed catheters have the advantage of being quite fast in that they are able to access remote portions of the body very quickly. They carry the obvious limitation that the catheter distal tip can only go where the blood flow is the highest. Furthermore, the catheters often are limited in the size of the "load" carried to the selected site. Said another way, balloon-less flow-directed catheters may be a marginal choice if a larger embolic coil or large diameter particle is to be delivered to the select site. One aspect of this invention involves the coating of catheters such as these to further improve their access rate.

On the other hand, over-the-wire catheters having variable stiffness, although quite strong and able to deliver embolic coils and large diameter particles through their large lumen, are comparatively quite slow in time of access. Friction with the interior of the guide catheter or the vessel path considerably slows the procedure time. However, the over-the-wire catheters can be directed to portions of the vasculature inaccessible to the flow-directed catheter. Lowering the resistance of the over-the-wire catheter to improve its lubricity and allow improved access time to remote body sites forms a further aspect of this invention.

This invention is generically a coated catheter having portions of differing flexibility which is suitable for the delivery of diagnostic, therapeutic, or vaso-occlusive agents or devices to potentially remote portions of the vascular system or other systems of open lumen within the body. The coating is significantly slipperier than other known coatings and is very durable.

This invention also includes a method of coating catheters using lubricious hydrophilic polymers and a method for producing a thin layer of such polymers on polymeric substrates.

The invention also includes a method for placing the catheter at the target site and a method for delivering diagnostic, therapeutic, or vaso-occlusive agents or devices to the target site.

SUMMARY OF THE INVENTION

This invention is a coated catheter for placement within a tortuous, small vessel pathway and a method for delivery of an agent or device to a target site. The coating is very slippery and quite durable. The catheter may be directed to the target site either by means of the blood flow to that site or by the use of a guidewire. The catheter has an elongate tubular body having proximal and distal ends and a lumen extending between the ends through which the diagnostic, therapeutic, or vaso-occlusive agent or device is delivered. Where appropriate, the lumen may be used for passage of a guidewire.

The elongate tubular body typically is formed of (a) a relatively stiff and, perhaps, tapered proximal segment, (b) a relatively flexible distal segment, and (c) a transition or intermediate section between the proximal and distal segments that is less flexible than the distal segment but more flexible than the proximal segment. At least the distal segment and, desirably, the transition segment of the catheter is treated with a lubricious, polymeric material. If so desired, all but the portion of the proximal section actually handled by the physician during final manipulation may be coated with the lubricious polymers.

The catheter bodies are coated with hydrophilic polymeric materials by a method involving application of the polymer from a dilute polymer or oligomer solution followed by simultaneous solvent removal and curing of the applied precursor. Multiple coatings of the polymeric material are contemplated.

DESCRIPTION OF THE INVENTION

Figure 1:
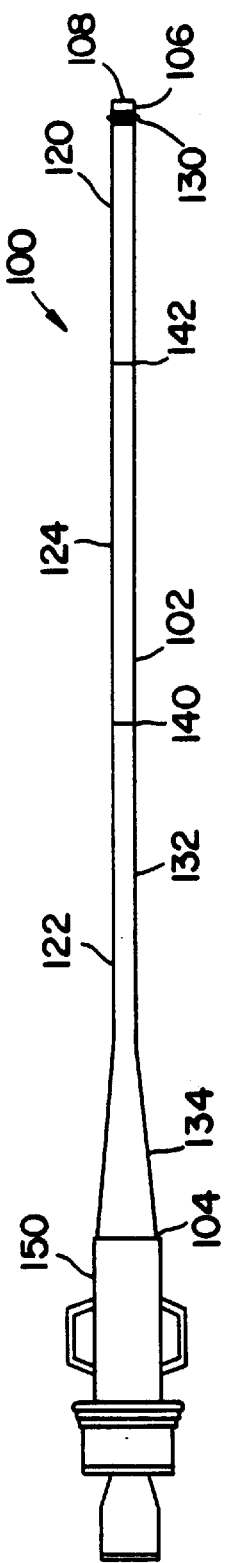
FIG. 1 is a diagram that shows an infusion catheter constructed according to a preferred embodiment of the present invention.

This invention is a catheter, optionally including a guidewire, having discrete sections of varying flexibility. In each variation of the invention, the catheter has a relatively stiff proximal section and a less stiff mid portion. For devices intended for use as flow-directed catheters, the distal end section is quite flexible; for devices intended for use with guidewires, the distal end section need not be quite as flexible since it need only follow the path of the guidewire without substantial disturbance of that pre-determined path.

At least the distal portion of the catheter is coated with a polymeric material to increase its lubricity and to minimize the potential for trauma as it moves through the body lumen. The mid or transition section of the catheter may also be coated with the polymeric material. The proximal section may also be coated although most desirably a small proximal end portion is left uncoated for increased control.

Particularly suitable as coatings in the catheter assembly of this invention are polymers or oligomers of monomers selected from ethylene oxide; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin. These monomers may be formed into homopolymers or block or random copolymers. The use of oligomers of these monomers in coating the catheter for further polymerization is also an alternative. Preferred monomers include ethylene oxide; 2-vinyl pyridine; N-vinylpyrrolidone and acrylic acid and its salts; acrylamide and acrylonitrile each polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred, because of their propensity for ease of linkage to the typical polymeric catheter substrates, are ethylene, propylene, styrene, and styrene derivatives.

Polymers or oligomers applied using the procedure described below are activated or functionalized with photoactive or radiation-active groups to permit reaction of the polymers or oligomers with the underlying polymeric surface. Suitable activation groups include benzophenone, thioxanthone, and the like; acetophenone and its derivatives specified as:

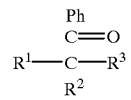

where
$R^1$ is H, $R^2$ is OH, $R^3$ is Ph; or
$R^1$ is H, $R^2$ is an alkoxy group including —$OCH_3$, —$OC_2H_3$, $R^3$ is Ph; or
$R^1=R^2$=an alkoxy group, $R^3$ is Ph; or
$R^1=R^2$=an alkoxy group, $R^3$ is H; or
$R^1=R^2$=Cl, $R^3$ is H or Cl.

Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the catheter body or other polymeric substrate by any of a variety of methods, e.g., by spraying a solution or suspension of the polymers or of oligomers of the monomers onto the catheter or by dipping the catheter into the solution or suspension (after sealing the open ends, if so desired). Initiators may be included in the solution or applied in a separate step. The catheter may be sequentially or simultaneously dried to remove solvent after application of the polymer or oligomer to the polymeric body and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as a coating for the catheter bodies discussed below are physical mixtures of homo-oligomers of at least one of polyethylene oxide; poly 2-vinyl pyridine; polyvinylpyrrolidone, polyacrylic acid, polyacrylamide, and polyacrylonitrile. The catheter bodies or substrates are preferably sprayed or dipped, dried, and irradiated to produce a polymerized and crosslinked polymeric skin of the noted oligomers.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for most polymeric substrates noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate. Movement through an irradiation chamber having an ultraviolet light source at 90–375 nm (preferably 300–350 nm) having an irradiation density of 50–300 mW/cm$^2$ (preferably 150–250 mW/cm$^2$) for a period of three to seven seconds is desired. Passage of a catheter through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

FIG. 1 shows an infusion catheter (100) constructed according to one embodiment of the invention. The catheter (100) has an elongate tubular body (102) with proximal (104) and distal (106) ends and an open inner lumen (108) extending between the ends. The elongate tubular body (102) has three segments; a relatively flexible and strong distal segment (120), a relatively stiff tapered proximal segment (122) and a transition section or segment (124) between the proximal and distal segments that is less flexible than the distal segment (120) but more flexible than the proximal segment (122).

The elongate tubular body (102) has a strong distal segment (120) which is desirably relatively flexible such that the catheter can easily navigate a tortuous vessel pathway. By "relatively flexible" is meant that a force of about 1×10$^{-4}$ pounds corresponds to a deflection of the material that is 10° from horizontal, or only about 5×10$^{-4}$ pounds of force to deflect the material about 80° from horizontal. By "relatively strong" is meant that the material has a burst pressure of greater than 195 psi, more preferably, the burst pressure is between about 195 and 220 psi.

The flexible distal segment (120) has an open end which allows for the infusion of diagnostic, therapeutic, or vasoocclusive agents into the target site. When the catheter is a flow-directed infusion catheter, the flexible distal segment (120) preferably is made of a polymer that is springy and biologically compatible such as low density polyethylene, polyurethane, a block copolymer of polyamide, polyvinyl chloride, or silicone or blends of the above.

The flexible distal segment (120) may carry one or more radiopaque bands (130) or may be doped with a radiopaque material such as barium sulfate, bismuth trioxide, bismuth carbonate, tungsten, tantalum or the like so that the location of the distal region of the catheter within the vessel may be visualized radiographically. The distal segment (120) typically makes up between about 5 and 25% of the total length of the tubular member and is between about 5 and 40 cm long, preferably between about 10 and 20 cm long. The inner diameter of the distal segment (120) may be between about 0.25 and 0.50 mm, more preferably between about 0.25 and 0.35 mm. The outer diameter of the distal segment may be between about 0.50 and 0.80 mm, more preferably between about 0.60 and 0.70 mm. The wall thickness of the distal segment 120 is between about 0.1 and 0.3 mm.

The proximal segment (122) of the elongate tubular body (102), when used as a flow-directed infusion catheter, is relatively stiff such that it can be easily pushed thus eliminating the need for guidewire support. The proximal segment (122) may be made of a polymeric or metallic material that is relatively stiff and biologically compatible such as high density polyethylene, polypropylene, Nylon, polyurethane, polyimides, polyvinyl chloride, polysulfones, polyfluorocarbons, polyethylene terephthalate, their mixtures, copolymers; or polyester elastomers or a braided shaft (a polymer outer core with a metallic mesh inner core). The proximal segment (122) may comprise a tapered proximal section (134) for attachment to the proximal end fitting (150) and a distal section (132). The proximal section (134) of proximal segment (122) may make up between about 60% and 80% of the total length of the tubular member (102) and typically is between about 90 and 130 cm long, preferably between about 100 and 120 cm long. The largest inner diameter of the proximal section (134), measured at the proximal end (104) of the tubular member 102, is often between about 0.40 and 0.60 mm, more preferably between about 0.45 and 0.55 mm. The outer diameter of the proximal section (134) at the proximal end (104) of the tubular member (102) is between about 0.8 and 1.2 mm. The wall thickness of the proximal section (134) of proximal segment (122) is between about 0.1 and 0.4 mm, more preferably between about 0.2 and 0.3 mm.

The distal section (132) of proximal segment (122) makes up between 10 and 20% of the total length of the tubular body (102) and is between about 20 and 40 cm long, preferably between about 20 and 30 cm long. The inner diameter of the distal section (132) of proximal segment (122) may be between about 0.20 and 0.50 mm, more preferably between about 0.25 and 0.35 mm. The outer diameter of the distal section (132) of proximal segment (122) is between about 0.60 and 0.90 mm, more preferably between about 0.60 and 0.70 mm. The wall thickness of the distal section (134) of proximal segment (122) is typically between about 0.1 and 0.3 mm.

The transition section (124) of the elongate tubular body (102) is less stiff than the proximal segment (122) but more stiff than the distal segment (120). A suitable material that is biologically compatible is a polymer such as polyurethane, a block copolymer of polyamide, polyvinyl chloride or silicone with greater durometer reading (i.e. that is stiffer) than the flexible distal segment (120). The transition section (124) may be radiopaque and thus observable in the event that the catheter becomes lodged in a particular portion of the vasculature or buckles. The polymeric material may be doped with a radiopaque material such as barium sulfate, bismuth carbonate, bismuth trioxide, tungsten, tantalum or the like. The transition section (124) may make up between about 10 and 20% of the total length of the tubular member (102) and is between about 20 and 40 cm long, preferably between about 25 and 35 cm long. The transition section (124) may be of constant diameter or may be tapered. The inner diameter of the transition section (124) may be between about 0.20 and 0.50 mm, more preferably between about 0.20 and 0.35 mm. The outer diameter of the transition section (124) may be between about 0.50 and 0.90 mm, more preferably between about 0.60 and 0.70 mm. The wall thickness of the transition section (124) may be between about 0.1 and 0.3 mm.

The proximal segment (122), transition section (124), and distal segment (120) are joined at junctions (140) and (142), respectively. The junctions may be formed by flaring, overlapping, and heat fusing the materials of the proximal segment (122) and transition section (124) and the transition section (124) and distal segment (120). Other methods for forming the junction, e.g., heat welding, solvent welding, etc. are also suitable. The distal segment (120), transition section (124) and distal section (132) of proximal segment (122) may all have approximately the same outside diameter or the transition section (124) and the distal section (132) of the proximal segment (122) may be tapered.

A standard proximal end fitting (150) is attached to the proximal end (134) of the proximal segment (122) often by heat fusion with reinforcing tubing.

Figure 2:
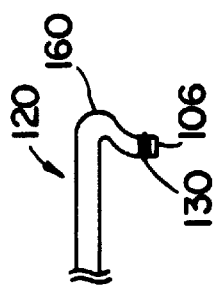
FIG. 2 is a diagram that shows the distal end on one embodiment of a flow-directed infusion catheter of the present invention in which the distal end is formed in an "S" shaped configuration.

FIG. 2 shows an embodiment of the distal segment (120) of the catheter where the tip (160) of the catheter is pre-shaped by heating with steam so that the distal end (106) points towards the wall of the vessel rather than in the direction of blood flow to increase the ease of manipulation through the tortuous vessel pathway. The particular embodiment shown is an "S" shape, but the tip may be any shape that allows for access to the particular vasculature being treated. One additional shape is that of a hockey stick. In this way, if the catheter becomes lodged against the vessel wall, the infusion of liquid through the catheter propels the distal end (106) of the catheter away from the vessel wall. Since the stiff proximal segment (122) is pushed, the distal segment (120) will be carried by the blood flood to the target site.

The catheter described above is useful in delivering diagnostic, therapeutic, or vaso-occlusive agents and devices to deep tissue, usually without need for a guidewire.

Figure 3:
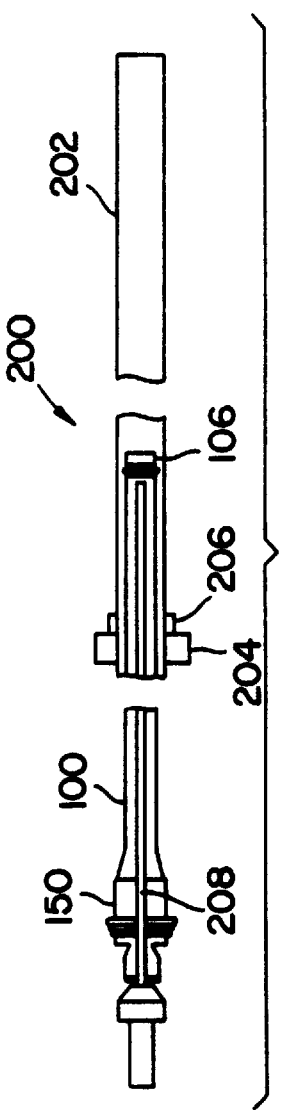
FIG. 3 is a diagram showing a flow-directed infusion catheter, stylet, and guiding catheter assembly.

FIG. 3 shows a catheter assembly (200) for placing the infusion catheter (100) at the target site. An appropriate guiding catheter (202) is inserted into the vasculature using standard placement techniques. A rotating hemostatic valve (204) may be utilized by connection to the guiding catheter luer adapter (206). The guiding catheter (202) is continuously flushed with saline. The thumb-screw of the valve (204) is opened and the infusion catheter (100) is inserted through the rotating hemostatic valve (204). Optionally, as shown in FIG. 3, a Teflon-coated stainless steel stylet (208) is first inserted into the flow-directed infusion catheter (100) in order to prevent kinking of the infusion catheter (100) within the valve (204). The distal end (106) of the infusion catheter (100) is advanced proximal to the tip of the guiding catheter (202). The stylet (208) is then removed from the infusion catheter (100). Once the stylet (208) is removed, the infusion catheter (100) is pushed out of the guiding catheter (202). The flow-directed infusion catheter (100) is gently guided by the flow of blood in the vasculature to the target site. Optionally, gentle pushing and pulling and injection of saline or contrast medium through the catheter lumen (108) may aid in the placement of the catheter at the target site.

Once at the target site, the desired agent is injected. Such agents may include radiopaque agents for viewing blood vessel anatomy and blood flow characteristics in the target region, vaso-occlusive agents which can be used to produce small-artery vaso-occlusion in the tissue region supplied by the target vessel, and pharmacological agents, such as anti-tumor drugs or sclerosing agents such as alcohols, which are effective against identified disease states at the target site. Vaso-occlusive agents useful in the treatment of arteriovenous malformations include polymers that are activated in the presence of polar solvents such as water and include materials such as n-butylcyanoacrylate. Other types of vaso-occlusive agents useful in the treatment of arteriovenous malformations include polymer solutions that coagulate by diffusion of the solvent when in contact with blood. Polyvinyl acetate dissolved in dimethylsulfoxide is one such agent. Alternatively, vaso-occlusive coils may be injected into the infusion catheter and delivered to a target site to occlude the blood flow at that site.

Figure 4:
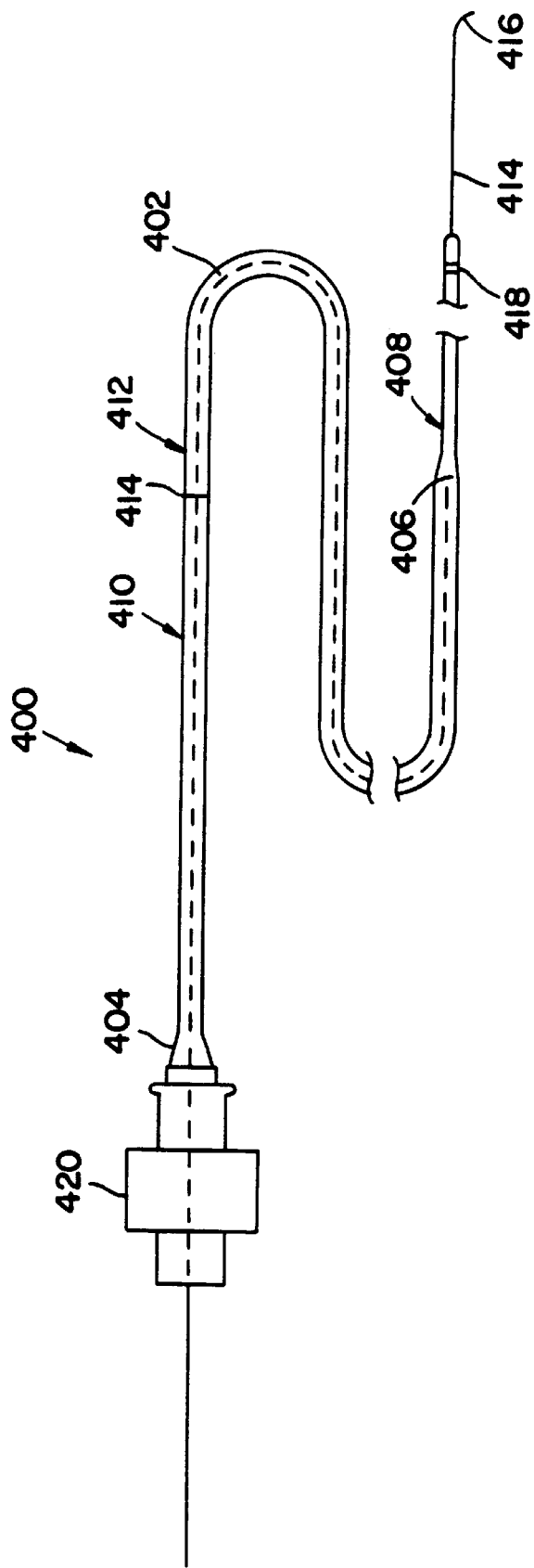
FIG. 4 is a side view of a typical catheter assembly according to this invention adapted for use with a guidewire.

FIG. 4 shows a variation of the invention in which the catheter is guided to its intended site by the use of a guidewire rather than through the use of blood flow. As with the device described above, the catheter assembly (400) includes an elongate member (402) having a proximal end (404) and a distal end (406) and an inner lumen which extends between those two ends. The elongate tubular body (402) has three segments; a relatively flexible distal segment (408), a relatively stiff proximal segment (410) and a transition section or middle segment (412) (separated at junction (414) from the proximal segment) between the proximal and distal segments that is less flexible than the distal segment (408) but more flexible than the proximal segment (410). Found within the lumen of the catheter assembly is guidewire (414) often having a bent tip (416) to allow ease of passage through the vasculature. Typically, such a catheter will have a small radiopaque band (418) of gold, platinum, palladium, or the like to permit monitoring of the catheter tip's position in relation to the tip of the guidewire or, when the guidewire is not in the catheter, to the vasculature itself. A standard proximal end fitting (420) may attached to the proximal end (404) of the proximal segment (410) often by heat fusion with reinforcing tubing. As is described in U.S. Pat. No. 4,739,768, to Engelson, the variation of flexibility may be introduced into the catheter assembly by use of sections of discrete coaxial tubing, e.g., by use of an inner stiff tube of polypropylene or high density polyethylene covered by a flexible tube of low density polyethylene or silicone in the proximal section (410) with the inner tubing junction found at (410). A thinner wall inner tubing of the same polymer as found in the proximal section (410) may be used as the inner tubing in middle section (412) to provide decreased stiffness in the middle section (412). In such an instance, the outer coaxial layer could be of the same composition and dimensions from proximal end (404) to distal end (406). Other methods of varying the stiffness to provide for strength at the proximal end, extreme flexibility at the distal end to allow conformance to the contortions of the guidewire through multiple flexions, and a middle section of strength sufficient to transmit pressure and torque from proximal end to distal end without buckling or compression. The various sections (particularly the inner section) may be tapered to provide variable stiffness through at the section or throughout the catheter.

EXAMPLE

Two sets of catheters were made, one according to the invention and one with a silicone coating, for comparison of the resulting slipperiness and durability of the coating. The catheters had three discrete sections: A proximal section of low-density polyethylene laminated over polypropylene tubing (having 0.022" I.D. and 0.039" O.D.) of 115 cm. length, a transition section of low density polyethylene laminated over polypropylene tubing (having 0.022" I.D. and 0.036" O.D.) of 15 cm., and a distal section of low density polyethylene of 20 cm. The low density polyethylene outer covering was a single piece covering throughout the length of the catheters.

The inventive catheter coating was produced using the following procedure:

a) catheters were dipped into a dilute polymeric solution of XX% polyvinylpyrrolidone and XX% polyacrylamide (each having photoactive groups) in a solution of isopropanol and water, and removed from the solution at a rate of 0.7"/sec., b) the coating was dried using heated air at 100° C., c) the coated catheter was exposed to ultraviolet light (100 mW/cm$^2$) for seven seconds to bond the coating to the catheter substrate and to crosslink the polymers in the solution, and d) steps a), b), and c) were repeated three times.

The comparative silicone catheter coating was applied using the following procedure:

a) catheters were dipped into a silicone solution of 1.5 ml Dow-Corning MDX 4-4159, 160 ml Freon, and 40 ml isopropanol.

b) the coating was cured at 60° C., c) the catheters were then coated with a silicone fluid solution (15 ml Dow 360 in 160 ml Freon), and d) the catheters were then air-dried for 30 minutes.

The catheters were separately introduced into a USCI Angiographic Systems Berenstein J-tip guiding catheter in a test rig allowing measurement of the force needed to push and to pull the catheters through the guiding catheter. Each of the catheters was tested through 20 pulls and pushes of 2 inches pushed and pulled at a rate of 1 inch/minute. In this way both absolute force needed to introduce the catheter may be recorded as well as the magnitude of all deterioration in the slipperiness. The measurements were taken for both the midsection and for the distal sections of the two catheters.

TABLE

| Pull. No. | Force (in lbs.) | |
|---|---|---|
| | Comparative | Invention |
| MIDSECTION | | |
| 1 | 0.044 | 0.025 |
| 20 | 0.054 | 0.025 |
| DISTAL SECTION | | |
| 1 | 0.023 | 0.013 |
| 20 | 0.027 | 0.013 |

It is apparent that the force needed to move the inventive catheter through the guiding catheter was only about half of that needed to move the comparative device. Additionally, the amount of force needed to move the comparative catheter increased substantially during the repetitive testing indicating that the coating was failing. In contrast, the inventive coating did not degrade during the test.

Although preferred embodiments of the invention have been described herein, it will be recognized that a variety of changes and modifications can be made without departing from spirit of the invention as found in the claims which follow.

We claim as our invention:

1. A catheter assembly, said catheter comprising an elongate tubular member having proximal and distal ends and an inner lumen extending between said ends, said member comprising:

(a) a relatively stiff proximal segment comprising a material selected from the group consisting of polyethylene, polypropylene, Nylon, polyvinyl chloride, polyethylene terepthalate, polyester elastomer tubing, a polymer outer core with a metallic mesh inner core, and laminates thereof;

(b) a relatively flexible distal segment; and (c) a transition section between said proximal and said distal segments that is less flexible than the distal segment but more flexible than the proximal segment, wherein at least the distal segment has been coated with a lubricious coating consisting essentially of a lubricity-causing polymer or oligomer comprising monomers of polysaccharides.

2. The catheter of claim 1 where the distal and the transition segment are coated with said lubricious coating.

3. The catheter of claim 1 where at least a portion of the proximal segment is coated with said lubricious coating.

4. The catheter of claim 1 wherein the distal segment has a burst pressure of at least about 195 psi and is made of a material which will show a force of about $10^{-4}$ pounds or less when ten centimeters of the material is deflected 10° from horizontal.

5. The catheter of claim 1 wherein the burst pressure of the distal segment is between about 195 and 220 psi.

6. The catheter of claim 5 wherein the distal section is made of a material having a deflection force of about $10^{-5}$ pounds or less for each 1° of deflection of the distal section.

7. The catheter of claim 1 wherein the distal segment is made of a polymeric material selected from the group consisting of polyethylene, polypropylene, polyurethane, a block copolymer of polyamide, polyvinyl chloride, silicone and blends thereof.

8. The catheter of claim 1 wherein the polymeric material of the distal segment is doped with a metallic material selected from the group consisting of barium sulfate, bismuth trioxide, bismuth carbonate, tungsten, and tantalum.

9. The catheter of claim 1 wherein the transition section is made of a polymeric material selected from the group consisting of polyethylene, polypropylene, polyurethane, a block copolymer of polyamide, polyvinyl chloride, and silicone, and laminates thereof.

10. The catheter of claim 9 wherein the polymeric material of the transition section is doped with a radio-opaque material selected from the group consisting of barium sulfate, bismuth trioxide, bismuth carbonate, tungsten, and tantalum.

11. The catheter of claim 1 in which the monomers of polysaccharides are selected from amylose, pectin, amylopectin, alginic acid, or crosslinked heparin.

* * * * *